(12) United States Patent
Lindstrand (10) Patent No.: US 8,599,371 B2
(45) Date of Patent: Dec. 3, 2013

(54) METHOD OF AND APPARATUS FOR OBTAINING HIGH DYNAMIC RANGE SPECTRALLY, SPATIALLY AND ANGULARLY RESOLVED RADIATION DATA

(76) Inventor: Mikael Lindstrand, Matfors (SE)

( * ) Notice: Subject to any disclaimer, the term of this patent is extended or adjusted under 35 U.S.C. 154(b) by 382 days.

(21) Appl. No.: 12/812,646

(22) PCT Filed: Jan. 23, 2009

(86) PCT No.: PCT/SE2009/000028
§ 371 (c)(1),
(2), (4) Date: Jul. 13, 2010

(87) PCT Pub. No.: WO2009/093961
PCT Pub. Date: Jul. 30, 2009

(65) Prior Publication Data
US 2011/0102784 A1    May 5, 2011

(30) Foreign Application Priority Data
Jan. 24, 2008    (SE) ...................................... 0800176

(51) Int. Cl.
*G01J 1/10* (2006.01)
*G01N 21/55* (2006.01)
*G01B 11/30* (2006.01)

(52) U.S. Cl.
USPC ......... 356/243.4; 356/445; 356/601; 356/612

(58) Field of Classification Search
None
See application file for complete search history.

(56) References Cited

U.S. PATENT DOCUMENTS

| | | | | |
|---|---|---|---|---|
| 4,253,765 A | * | 3/1981 | Kato et al. | 356/328 |
| 4,588,897 A | * | 5/1986 | Inbar et al. | 250/363.07 |
| 5,168,532 A | * | 12/1992 | Seppi et al. | 382/270 |
| 5,272,518 A | * | 12/1993 | Vincent | 356/405 |
| 5,519,204 A | * | 5/1996 | Rudd et al. | 250/205 |
| 5,546,189 A | * | 8/1996 | Svetkoff et al. | 356/602 |

(Continued)

FOREIGN PATENT DOCUMENTS

| | | | |
|---|---|---|---|
| JP | 03010125 A | * | 1/1991 |
| JP | 11008734 A | * | 1/1999 |
| JP | 2008252157 A | * | 10/2008 |
| WO | 03067420 A1 | | 8/2003 |

OTHER PUBLICATIONS

Naya, S.K. et al., "Adaptive Dynamic Range Imaging: Optical Control of Pixel Exposures Over Space and Time," Proceedings of the Ninth IEEE International Conference on Computer Vision (ICCV'03), pp. 1-8, 2003.*

*Primary Examiner* — Gordon Stock, Jr.
(74) *Attorney, Agent, or Firm* — David A. Guerra (57) ABSTRACT

A method of obtaining high dynamic range, spectrally, spatially and angularly resolved radiance of a sample surface of a sample by an electromagnetic irradiator irradiating electromagnetic radiation of controlled spectral distribution onto the sample surface and, using an electromagnetic sensitive sensor to register the reflected spectral distribution. The spectral distribution of the intensity of the electromagnetic field is modeled to have been reflected by a plurality of spatially well defined part-surfaces of the sample surface. The electromagnetic sensitive sensor being well-defined in terms of the functional dependency between input radiation and output signal and the registering exposure time-period being selected individually for each individual sensor element, such as to compile an information volume that represents the registered high dynamic range spectrally resolved electromagnetic radiance as a function of the position of the part-surfaces within the sample surface and of the respective angle enforced on the sample while measuring.

19 Claims, 4 Drawing Sheets

(56) References Cited

U.S. PATENT DOCUMENTS

| | | | |
|---|---|---|---|
| 5,933,190 A * | 8/1999 | Dierickx et al. | 348/302 |
| 6,061,091 A * | 5/2000 | Van de Poel et al. | 348/241 |
| 6,221,569 B1 * | 4/2001 | Ishikawa | 430/359 |
| 6,496,280 B2 * | 12/2002 | Ishikawa et al. | 358/1.9 |
| 7,286,215 B2 * | 10/2007 | Imura | 356/229 |
| 7,381,936 B2 * | 6/2008 | Tan et al. | 250/208.1 |
| 7,777,804 B2 * | 8/2010 | Shan et al. | 348/362 |
| 8,073,234 B2 * | 12/2011 | Harris et al. | 382/141 |
| 2004/0036775 A1 * | 2/2004 | Watson et al. | 348/207.1 |
| 2004/0057060 A1 * | 3/2004 | Johannesson et al. | 358/1.9 |
| 2004/0239798 A1 * | 12/2004 | Nayar et al. | 348/362 |
| 2006/0065857 A1 * | 3/2006 | Lex | 250/559.4 |
| 2006/0175537 A1 * | 8/2006 | Hiramatsu | 250/208.1 |
| 2009/0002555 A1 * | 1/2009 | Barnhoefer et al. | 348/554 |
| 2011/0079705 A1 * | 4/2011 | Tomaney et al. | 250/208.1 |
| 2012/0013779 A1 * | 1/2012 | Hattery et al. | 348/302 |
| 2012/0019693 A1 * | 1/2012 | Goma et al. | 348/246 |
| 2012/0134603 A1 * | 5/2012 | Pang et al. | 382/294 |

\* cited by examiner

METHOD OF AND APPARATUS FOR OBTAINING HIGH DYNAMIC RANGE SPECTRALLY, SPATIALLY AND ANGULARLY RESOLVED RADIATION DATA

CROSS-REFERENCE TO RELATED APPLICATIONS

This application is an U.S. national phase application under 35 U.S.C. §371 based upon co-pending International Application No. PCT/SE2009/000028 filed on Jan. 23, 2009. Additionally, this U.S. national phase application claims the benefit of priority of co-pending International Application No. PCT/SE2009/000028 filed on Jan. 23, 2009, and Sweden Application No. 0800176-0 filed on Jan. 24, 2008. The entire disclosures of the prior applications are incorporated herein by reference. The international application was published on Jul. 30, 2009 under Publication No. WO 2009/093961.

FIELD OF THE INVENTION

The present invention relates to a method for obtaining radiance data. More precisely the invention is concerned with measuring and characterizing high dynamic range spectrally, spatially and angularly resolved radiance data, in one integrated optical system.

BACKGROUND OF THE INVENTION

The appearance of an object is a visual sensation caused by the light radiated from the object under study. The appearance is essentially a combination of features in a spatial domain and a tri-chromatic domain. Objects in general have a principally different appearance in different angular orientations, relative to the incident light source (electromagnetic radiator) and the observer (receptor). Common imaging devices, e.g. digital cameras and computer scanners resolve the spatial domain and usually the tri-chromatic domain. To also describe the angular dependent behavior, it is necessary to also include the angular degree of freedom in the characterization process. Capturing and characterizing a spatial, angular and tri-chromatic optical response of an object, forms a powerful basis when characterizing the objective causes for the appearance of an object.

One, of a number of technical challenges in this context, is that the angle resolved optical characterization of an object often involves a wide range of signal intensities (signal dynamics), including high intensity specular reflections and low intensity reflections from other orientations. Common units for image registration lack the ability to handle the high dynamic range of intensities normally present in the context and are therefore not suited for the task.

Characterizing the objective causes for the appearance of an object is of high industrial relevance e.g. when conducting product development within the paper industry. The product development may deal reducing certain deficiencies in a certain characteristic of the product, say undesired gloss variation. A characterization of the objective causes for the appearance of the product, including the undesired gloss variation, would be a vital help in the search of countermeasures to reduce the unwanted behavior. The characterization of the objective causes of the appearance of an object would increase the efficiency of product development efforts.

Known methods for characterizing the objective causes for the appearance of a product are not effective enough because the data gathered by these methods does not allow for an efficient characterization of high dynamic range spectrally, spatially and angularly resolved radiation data. As each and every of these characteristic features of the resulting information volume are vital, every characterization method that lacks at least one of these features will be a suboptimal characterization method. There is therefore a clear and apparent need for an improved method. Present invention meets this need. The present invention yields new relevant information that facilitates finding solutions to previously unsolvable problems. Alleviating problems associated with the characterization of data will contribute to more efficient product development efforts and finally in better and cheaper end products.

PRIOR ART

The applicant's Swedish patent SE511929 discloses a method and device for the determination of gloss quality from a sample surface of a sample by registering the intensity of reflected light together with spatial and angular information, and is hereby included as a reference. The known art, in part defined by the above mentioned Swedish patent SE511929, lacks two mutually critical characteristics, firstly A) the ability to also characterize spectrally resolved radiation (in the limited case: color), and secondly B) the ability to adequately characterize the normally large dynamic range of radiation associated with a goniometric characterization. The dynamics of the directed radiance intensities may cover more than six decades (values from 1 to $10^6$ units) for common and relevant sample surfaces. The problem with characterization of the high dynamic range of radiance is in part related to noise and distortion levels of common image sensing systems. To handle this problem, it is desirable to introduce a mathematically based model of the sensor system that describes the relation between input and output signals. In the literature of the more general discipline of signal theory and the more specific discipline of image analysis there are abundance of mathematical models of sensor systems, varying in part in the level of ambition. Below is described only some of the most relevant issues in this context of sensor system modeling. More advanced and refined mathematical models of the relation between input and output signals of sensor systems may be desirable for very demanding applications. Such models are described in the literature (disciplines of signal theory and image analysis). The most relevant issues in the context of mathematical modeling of the sensor system:

1. Nonlinear input-output response. Ideally the described sensor should show a relation between the input x and output $f(x)$: $f(x)=mx+b$, where m is a (constant) scalar and $b=0$. i) Sensors normally give a non-negligible output, although the input radiation is approximately zero in the wavelength region the receptor senses. The function is then at best a (non-desired) affine mapping where $f(x)=mx+b$ and b is non-zero. b is described, in some sensory system models to be caused by so called "dark current" (normally a function of in part the integration time) and so called bias (normally independent of the integration time). In this text, the model term b will for simplicity be called "dark current", where the bias is included implicitly. ii) Sensors may show a response between input x and output $f(x)$ other than a constant slope, hence the relation $f(x)=mx+b$ may not be described with m being a scalar. These deficiencies, i) and ii), may cause problems both for visualization, causing renderings of low quality, and for further calculations, as the nonlinearity may be described as distortion that lower the signal-to-noise ratio, causing the characterization to be less accurate. These deficiencies are normally more severe characterizing a high dynamic range signal than characterizing a signal of a lower dynamic range. These problems are more severe characterizing a high dynamic range input, than an input of more a more restricted dynamic range, and the issue is hence of high relevance to the present invention.

2. Nonlinear exposure time interval—output relation. During measurement, the sensor is exposed to radiation for a certain well defined time interval—the exposure time interval during which the amount of incidence light is integrated to yield the output value of the sensor. A spatially resolved sensor further has a number of sensor elements that individually contribute to the compound output. In general, the exposure time interval should be chosen wisely for the samples measured. A too long interval causes the sensor to saturate and will hence give an incorrect output. A too short interval causes the output to a large degree consist of as well dark current (noise and distortion) (see 1i above) as, so called, quantization distortion. Quantization distortion arises when a continuous signal (infinite level resolution and infinite temporal resolution representation) is represented with a finite number of levels at finite number of samples, i.e. a discrete signal. The ratio of quantization distortion is in average larger at low signal levels, assuming a linear digital representation. Also the input signal may be of a higher dynamic range than the sensor is able to cover, then the exposure time interval selection may be an optimization problem to limit the joint effect of errors due primarily to saturation, quantization distortion and noise. For these reasons it is desirable to have the possibility to vary the exposure time. However, varying the exposure time causes also the output to alter, longer integration time causes a higher signal output. Hence to be able to relate measurements of different exposure time intervals it is necessary that the relation between exposure time interval and signal output is known, so that this signal characterization effect can ideally be eliminated. If the relation is nonlinear, the most intuitive and most often used relation $f(x)=x/s$, where s is the exposure time will cause the characterization to be less accurate. These problems are more severe characterizing a high dynamic range input, than an input of more a more restricted dynamic range, and the issue is hence of high relevance to the present invention.

3. Error propagation due to saturation. Ideally, when a spatially resolved sensor saturates, only the saturated sub-part of the sensor should be affected. The saturated sub-part is easily identified by its output values reaching the maximum value for the sensor and the saturated sub-part may hence be eliminated. However, normally sensors do not show this desirable behavior. Contrary, when a certain sub-region of the sensor saturates, also a surrounding is affected, distorting the output values of this surrounding. The distorted surrounding is not easily identifiable and may unintentionally be included in the output, causing the characterization to be less accurate. These problems are more severe characterizing a high dynamic range input, than an input of more a more restricted dynamic range, and the issue is hence of high relevance to the present invention.

In general the discipline of sensing high dynamic range motifs is referred to as high dynamic range imaging, HDRI. The basic idea is to build one result image based of a number of temporary help-images, where the temporary help-images differ in the integration time under which they were imaged. Algorithmic transformations compensates for the characterized intensity level differences caused by the difference in integration time when constructing the result one image of the number of ingoing temporary help-images.

Approaches to handle high dynamic range imaging have presented, e.g. Nayar S K and Branzoi V, "Adaptive Dynamic Range Imaging: Optical Control of Pixel Exposures Over Space and Time", Proceedings of the Ninth IEEE International Conference on Computer Vision 2003, which is here included as an reference. This reference describes a high dynamic range imaging device based on a spatial light modulator. The described approach is based on a complex and expensive technical subsystem namely a chromatic spatial light modulator (SLM) able to handle high dynamic range signals. Such device is significantly more complex and expensive than the imaging hardware the present invention is based on. Besides using a complex and expensive imaging device for the high dynamic range imaging system, the Nayar-Branzoi approach lacks the critical feature of angular resolution. Given the high business demand for a device such as the current invention, it may be argued that the combination of described high dynamic range imaging device and angularly and spatially resolved measurement devices is not an obvious operation, even for the professional in the business. Another argument for the relevancy of the current invention is the high cost of the chromatic SLM used in the Nayar-Branzoi approach which would severely cripple the business applicability. The current invention may instead be based on common, in comparison, low priced CCD sensor which significantly increases the business applicability. However to use a conventional chromatic image sensor for high dynamic range imaging is a technological challenge, in part due to the error propagation of saturated sensor elements. The challenges involved using a CCD sensor, are solved by the current invention.

In general, the above described shortcomings A) and B) cripple the applicability and limits the potential industrial value of the known art.

OBJECTIVES OF THE INVENTION

One objective of the present invention is providing a method that is able to characterize high dynamic range, spatially and angularly resolved radiation data. This facilitates novel applications in a range of principally different areas of high significance for various industries, such as the paper industry.

Another objective of the present invention is to facilitate a spectrally resolved characterization of the high dynamic range angularly and spatially resolved radiation. The characterization is realized by using a spectrally well defined electromagnetic radiator and a receptor with a set of spectrally well defined channels. The characterization may consist of one or a number of measurements, the measurements differing in the spectral distribution of the radiator—which facilitates characterization of fluorescence materials.

Another objective of the invention is to select the radiation exposure time-period individually for each individual sensor element of the sensor, to facilitate the registration of the exceptionally large dynamic range of radiation, often related to the combination of the often high intensity specular reflections, and the often low intensity reflections from other measurement geometries.

BRIEF DESCRIPTION OF THE DRAWINGS

The invention will be described in more detail below with reference to exemplifying embodiments thereof and also with reference to the accompanying diagrammatic drawings, in which.

DETAILED DESCRIPTION OF THE INVENTION

Reference will now be made in detail to the present preferred exemplary embodiments of the invention, which are illustrated in accompanying drawings. Wherever possible, the same reference numbers will be used throughout the drawings to refer to the same or the like parts.

Figure 1:
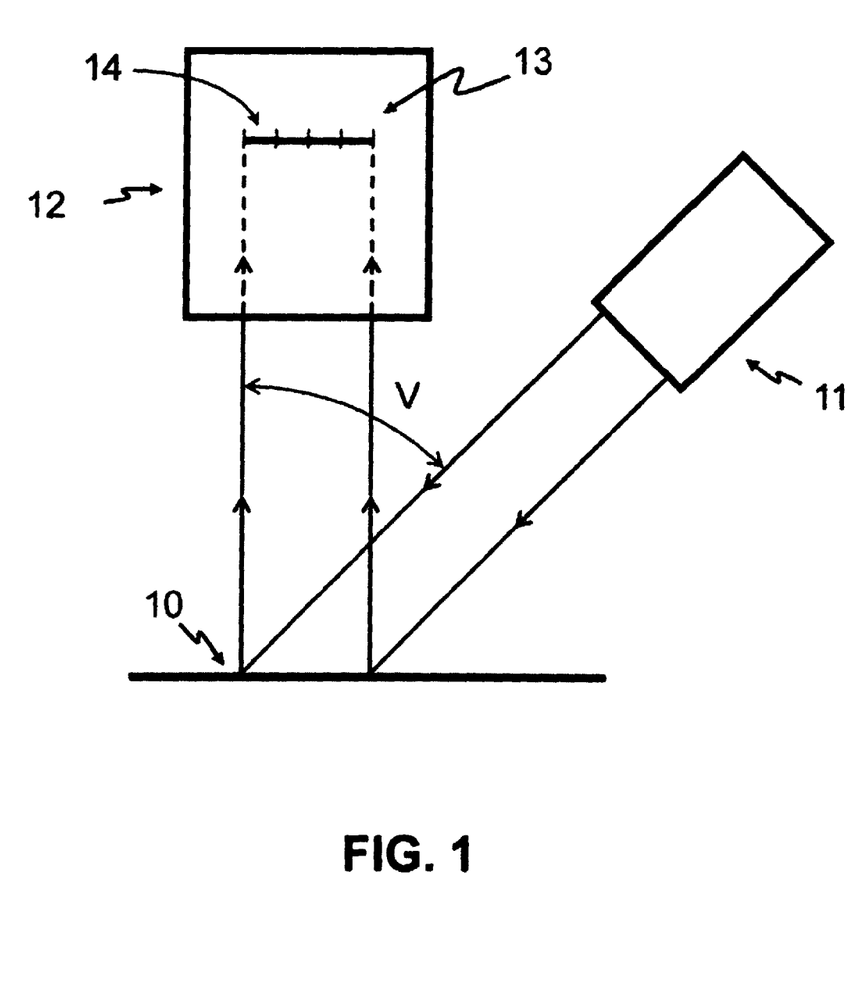
FIG. 1 is a perspective view of one possible apparatus according to the invention.

The method for obtaining high dynamic range spatially, angularly and spectrally resolved radiance of a sample surface of a sample, such as a paper sheet, can, referring to FIG. 1, be determined by using a irradiator 11, that may although not explicitly described in the figure, include optics that collimates the irradiation, spectral filter that changes the irradiation spectrum and polarization filter, irradiating electromagnetic waves of controlled spectral distribution onto the sample surface of a sample 10, and using a spatially resolved sensor system 12, consisting of a spatially resolved sensor 13 that in turn consists of a number of individual sensor elements 14. The sensor system 12 may, although not explicitly described in the figure, include optics that collimates the radiation, spectral filter that changes the radiation spectrum and polarization filter, and according to the below described high dynamic range procedure registering the spectral distribution of the electromagnetic field that reaches the sensor system 12 and more specifically the individual sensor elements 14. The angle V defined by the optical axis of the irradiator 11, and the optical axis of the sensor system 12 is in the given realization 45 degrees, although other angles for instance 0 degrees are possible. To attain spatially resolved information, a sequence of measurements has to be conducted, having a relative motion of at least one of the components: the irradiator 11, the sample surface of a sample 10, or the sensor system 12, relative to the others or the other of these three 10-12. Also must the projection errors caused by the relative inclination of the sensor system 12 and the sample 10 be retransformed, which may be done using commonly known suitable image analysis algorithm based on basic trigonometry.

Figure 2:
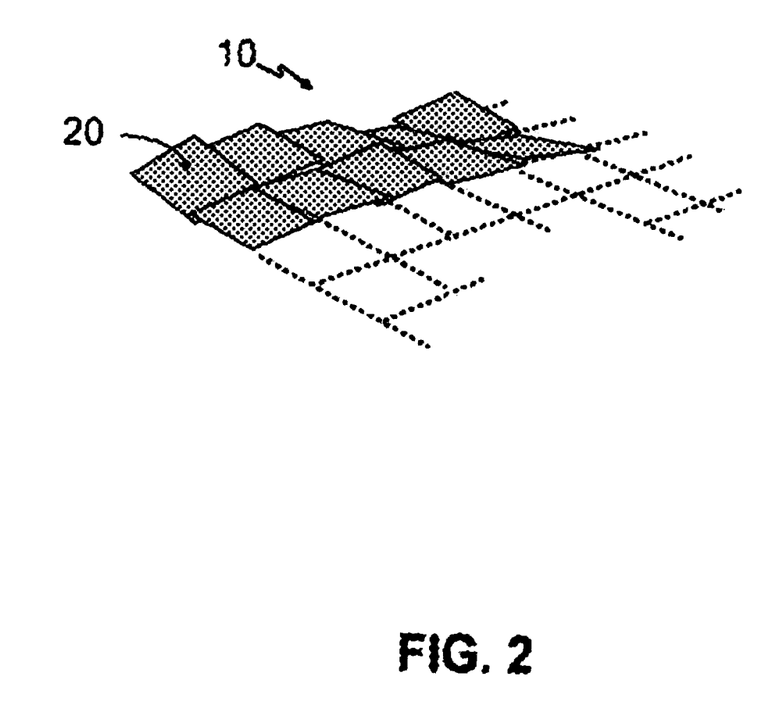
FIG. 2 illustrates a facet model of a sample surface of a sample.

FIG. 2 illustrates a model of a sample surface of a sample 10, consisting of a large number of part-surfaces 20. In the model these facets 20 bear information about inclination, reflectance and emittance characteristics.

When characterizing a sample surface of a sample 10, the registration exposure time-period can be selected individually for each individual sensor element 14 analyzing a certain part-surface 20 of the sample surface of a sample 10. Thereby an information volume may be compiled that represents the registered high dynamic range spectrally resolved electromagnetic intensity as a function of the position of a part-surfaces 20 within the sample surface of a sample 10 and of the respective angle enforced on the sample while measuring. In a strict sense, the term "volume" should be exchange with the expression "hyper volume" as the number of dimensions of the information set is larger than three; the information stored being spectrally resolved. Despite this, the information set is for reasons of convenience also in the following termed information volume.

The approach of selecting the exposure time individually comprises a number of critical preconditions in order to be successful, including (further described in detail below):

1. Characterization of the response curve of the sensor, which may be approximated by a characterization of: i) the dark current, i.e. characterizing b in the relation $f(x) \approx mx+b$; and ii) slope i.e optimizing m for the relation $f(x) \approx mx+b$, such that the function $z(x)=abs(f(x)-(mx+b))$ where abs( ) is the absolute value, is minimized when integrated over x.
2. Characterization of the response of the sensor as a function of the sensor exposure time.
3. Error propagation characterization—how do a saturated sensor element propagate to surrounding sensor elements.

The following description gives means to obtain the preconditions 1-3:

1i. The characterization of the dark current may be realized by measuring the sensor output while shielding the sensor from radiation, so that the sensor is exposed to only a negligible amount of radiation, of wavelengths that the sensor is sensitive to. Ideally the sensor should then produce a zero output, but this is normally not the case for physical (non-theoretical) sensors. The described characterization should ideally be performed individually for each individual sensor element 14, resulting a dark current image, but may alternatively be approximated as a mean value of all individual sensor elements 14, a dark current scalar. The described characterization should be performed individually for all relevant sensor exposure time intervals, or approximated by characterization of the dark current at a number of different exposure time intervals and interpolation of the other relevant dark current values. The dark current characterization is thereafter used for compensation of the sensor output—the sensor output is reduced by the corresponding dark current value and possible negative values are set to zero.

1ii. The characterization of the remaining (after the above described dark current reduction) transfer function may be performed inter alia by exposing the sensor in a range of different radiation intensities, while holding the spectral distribution of the radiation 11 constant, to thereby attain a relation between input radiation intensities and sensor output values. The characterization is performed for each spectral channel of the sensor.

2. The characterization of the response of the sensor as a function of the sensor exposure time may be performed by the following procedure:
   a. Choose the shortest possible exposure time, adjust the radiation intensity onto the sensor to reach a low dark current reduced sensor output, say in the range of 3-5 percent of the peak output.
   b. Hold the intensity of the irradiator 11 constant during the following procedure steps.
   c. Increase the exposure time in small increments and register the sensor output.
   d. Stop when the sensor output is saturated, and eliminate the corresponding exposure time-sensor output pair.

The described procedure generates the desired exposure time-sensor output relation.

3. The error propagation of saturation. The understanding of the error is facilitated by dividing it into two principally different sources of errors: circuit induced error propagation (often referred to as "bleeding") and scattering induced error propagation. Further, the approach chosen for characterizing the error propagation depends on the type of sensor used. A) If the sensor system 12 has one sensor for each spectral channel or, similarly uses spectral (chromatic) and spatially global (one filter covers all the sensor elements 14 of the sensor 13), the characterization may be performed using the following approach: create an approximation to a radiant point source at an infinite distance, e.g. using a collimated flood radiator with a shielding mask with only a minimal hole that admits radiation transmission. The point source (hole of the mask) should be smaller that the corresponding dimension covered by one individual sensor element 14 on the sample. By characterizing the point source at a variety of relevant intensity higher than the intensity causing the sensor element that covers the point source in its detection field to saturate, the error propagation for the system may be characterized. B) If the sensor has an integrated spectral selective mosaic to create the spectral selectivity, the error propagation of saturation will cause certain pronounced unwanted color distortion effects that may be utilized during the characterization of the system. The characterization may be performed using the following approach: As error propagation will influence surrounding pixels that correspond to other colors, the error propagation characterization is facilitated by studying the change of color pattern (for a static motif) as a function intensity level in the sensor. Most physical (real world) sensors have different sensitivity of the different color channels (before compensation). Assuming such difference in color channel sensitivity and using an object that irradiates an energy spectrum that is, at each given spatial position, approximately equal for the corresponding spectral channels of the sensor (corresponding to only gray scale in the special case of visible light). The irradiated energy of the object should further vary from low intensity to high intensity (corresponding to a gray scale variation from near-black to near-white in the special case of visible electromagnetic radiation) within the area covered by the sensor 13. With the described preconditions, sensing the object under a non-saturated sensor, the output will at each position be positive but not equal for each spectral channel, due to the difference in sensitivity of the spectral channels of the sensor. When increasing the intensity of the irradiator saturation will occur, including error propagation to adjacent sensor elements. As saturation will yield an underestimation of the true value in the given sensor element and as error propagation to adjacent sensor elements will yield an overestimation of the adjacent sensor elements of other spectral bands, the two-fold effect is a pronounced change in color already for minute error propagation, a distortion in color due to the saturation error propagation. The amount of color distortion may be characterized, e.g. by an ordinary Root Mean Square (RMS) distance measure. By assuming an arbitrarily chosen error propagation surrounding, and using that surrounding in the exclusion of incorrect sensor element values, in the imaging process of the temporary help-images, a result image is generated based on the assumed error propagation surrounding. A number of result images may be generated based on an equal amount of different assumed error propagation surroundings and their signal-to-noise performance may be estimated. If it may be assumed that the error propagation surrounding is limited to few sensor elements, e.g. a distance corresponding to say 10 sensor elements, the number of likely (based on the aforementioned two principal causes of the error propagation) error propagation surroundings are relatively few, in the order of tenths, and easily evaluated in terms of distortion, using the mentioned distance measure.

> Comment: in the search of an optimal error propagation exclusion surrounding, if the surrounding is chosen too small, incorrect error propagation affected sensor values will be included in the temporary help-images and hence the result image, causing the distortion to increase. If the selected error propagation exclusion surrounding is chosen too large, an unmotivated amount of sensor values, including correct values, are excluded from the temporary help-images, which limits the potential of the imaging algorithm, causing the signal to noise ratio of the image to decrease causing the distortion to increase. Hence when choosing either a too small or a too large error propagation exclusion surrounding, distortion will increase. Therefore it is likely that it is possible to reach an optimum, at a minimal distortion level, when choosing the size of the error propagation exclusion surrounding.

With the described three preconditions met, the invention may be realized by the following approach: For a given object scene and using imaging optics, let the individual sensor element 14 be exposed to the radiation from the scene to get an intensity value $I_1$ under the duration of either a) the time-period $T_1$ when the individual sensor element 14 have reached a predefined (high) value $I_1=I_H$ or b) the predefined maximum time-period of exposure (also called integration time) value, $T_{MAX}$ is reached, whichever is the shortest of $T_1$ and $T_{MAX}$. This will cause the sensor elements to, in general, use different exposure time-periods, on a sensor element individual basis. The individual sensor element 14 outputs can thereafter, using the preconditions already described, be transformed using: 1) compensation for the appropriate dark current value, 2) compensation for the exposure time-period used, in either the case 2a) $I_1=I_H$, or in 2b) $T_{MAX}$ has been reached ($I_1<I_H$); all these are performed for the individual sensor elements.

Performing the described compensations for all the individual sensor elements 14 of the sensor will yield a high dynamic range sensor output. Perform one high dynamic range sensor output each for every spectral channel of the sensor. The described algorithm facilitates a spectral high dynamic range imaging device that in combination with a spatially and angularly resolved characterization methodology is able to perform a high dynamic range spectrally, spatially and angularly resolved radiation characterization. Using a less ambitious approach the individually integrated time-periods possible to choose from is limited to a few, say four. These four different part-images are generated, using four different integration time-periods. This approach may result in a number of different saturated sensor elements 14, for the images corresponding predominately to the longer integration time intervals. The previously described characterization of the error propagation guides determines what areas to exclude in the measurement. The sequence of acquiring different integration time-periods can thus be realized in different ways. Given above, are two examples: 1) by sensor element individual selection, appropriate when a nearly continuously variable integration time may be selected, and 2) batch registration of a set of temporary help-images, where the integration time differs between the images, appropriate when the registration is limited to only a few number of different integration time intervals, or when the sensor system 12 do not provide the ability to individually control the sensor element 14 integration time.

Figure 3:
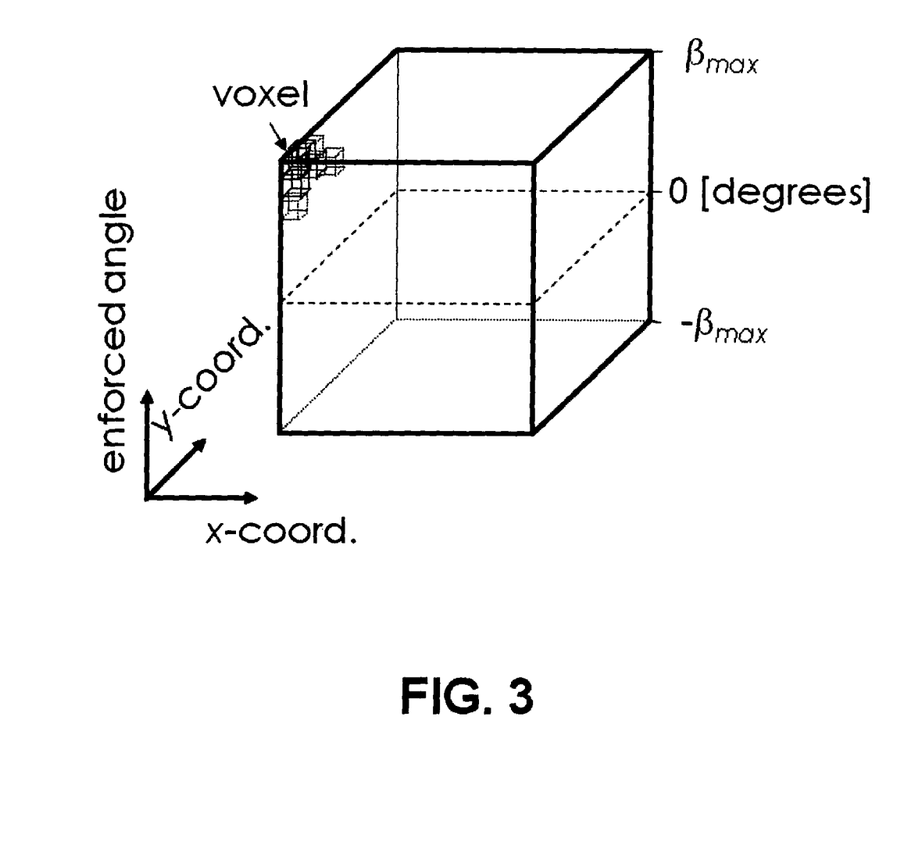
FIG. 3 is a simplified graphic presentation of an information volume.

FIG. 3 illustrates data stored in the form of an information volume intended for use as a representation of the electromagnetic reflection and emission properties of a sample surface of a sample 10, more specifically a function I=f(x,y,z), where I represents the measured spectrally resolved electromagnetic reflection in the coordinate (x, y, z). The x-y-dimensions represent the position within the sample surface of a sample 10 and the z-dimension represent the angle enforced on the sample while measuring, and z-values ranging from $-\beta_{MAX}$ to $\beta_{MAX}$, where the enforced angle of 0 degrees corresponds to a smooth glossy sample being oriented such that it globally shows specular reflection. At the global specular reflection the optical axis of the irradiator 11 and the mean normal to the sample surface of the surface 10 are in the given example forming a −22.5 degree angle; and similarly the optical axis of the imaging system 12 and the mean normal to the sample surface of the surface 10 are forming a 22.5 degree angle. Although the range of z-values is in the given example is showing a symmetric range around zero it may not always be preferable. In the given example in FIG. 3, $\beta_{MAX}$ corresponds to approximately 55 degrees. Each given triplet $<x_i, y_j, z_k>$ hence defines a volume element, or a so-called voxel (c.f. pixel). The reflection and emission properties may possibly be registered using a spectral basis of low dimensionality, e.g. three dimensions where one instance is the in image sensing and computer context common RGB-basis, where another instance of such triplet is the for visual perception application more appropriate CIE XYZ-basis, or another appropriate representation having three or another number of dimensions. Another possible and somewhat more sophisticated strategy to achieve compression is to perform a more rigorous spectrally resolved measurement of the radiation characteristics of a sample surface of a sample, and then to perform the compression into a characterizing set of basis vector. These may inter alia be based on a Fourier basis, Wavelet basis or generated based on the, for the discipline of signal theory commonly used and for the current application appropriate concepts of eigenvectors and vector quantization. Yet another more sophisticated approach is to perform multiple repeated spectrally resolved measurements, using a narrow-bandwidth irradiator and using different irradiator midpoint wavelengths for the different performed multiple repeated measurements. The result is hence a high dynamic range, spatially and angularly resolved radiance factor matrix—a matrix information for each given voxel in the information volume—an exceptionally powerful optical information set that is able to meaningfully characterize a sample surfaces of a sample 10 showing as well diffractive optically variable image device (DOVID) effects, commonly in use in e.g. the document security industry, as fluorescence effects. In analogy with previous reasoning, the term "volume" is again in a strict sense inappropriate where "hyper volume" would be more correct as the dimensionality is again higher than three, in the last given example resolved also in terms of wavelength of excitation of the irradiator 11. Despite this, the information set is for reasons of convenience also in the following termed information volume.

Figure 4:
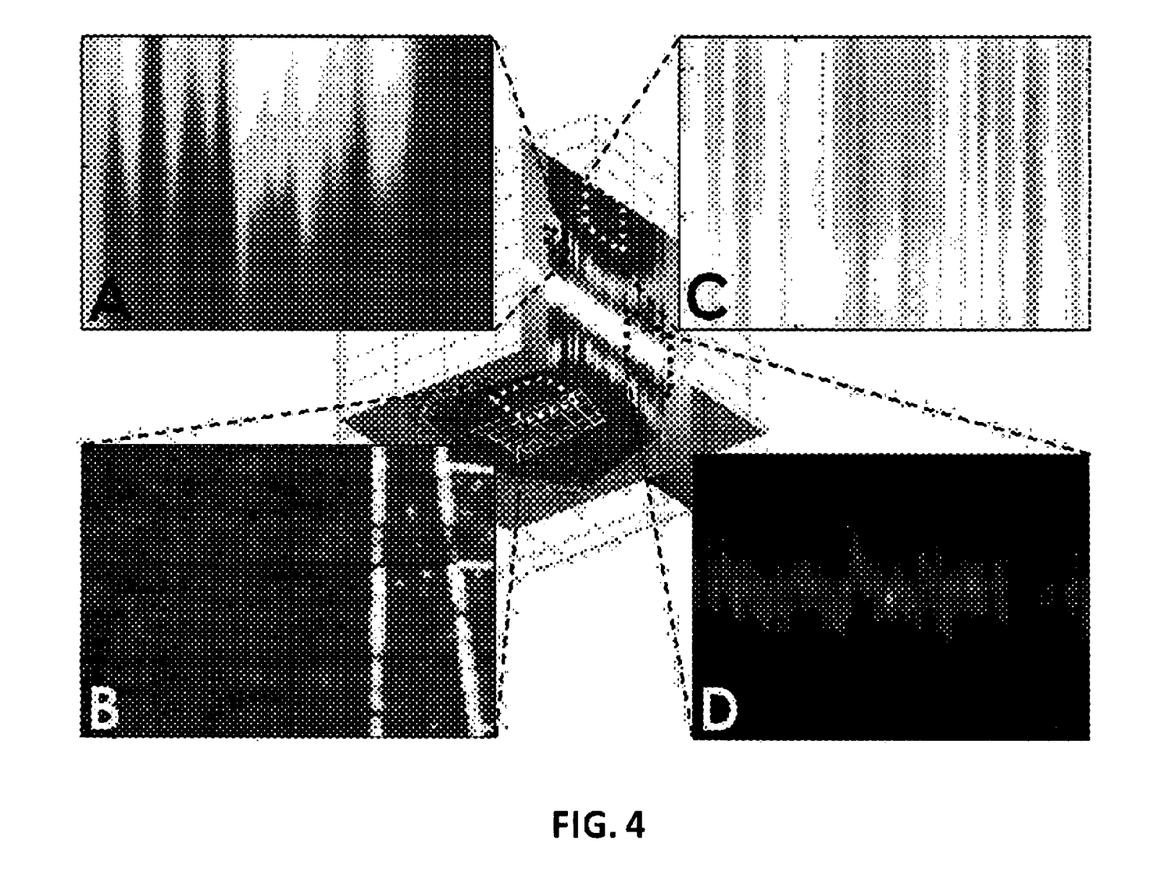
FIG. 4 is a visualization of an information volume generated according to the invention.

FIG. 4 is a visualization of an excerpt of an information volume generated according to the invention. NOTE: despite the characterization includes color information, the illustration is in black and white only, as the patent application regulations prohibit color illustrations. The sample surface area characterized do essentially not contain fluorescence material, hence the characterization can be described as the more limited reflection information volume. The characterized surface is a so called Diffractive Optically Variable Image Device (DOVID), branded as the Alphagram®, of a 500 Euro bank note. The figure aims at illustrating the principal features, including the resolution of the information volume. Note that all the sub-illustrations in this Figure stem from one and the same result information volume (i.e. not multiple characterizations e.g. adapted for different reflectance levels, etc.). In the background of the illustration, there are two orthogonal planes, one horizontal image plane and one vertical angular plane. Sub-illustration A: zoom-in of the angular plane, illustration of the high angular resolution of the characterization. Sub-illustration B: zoom-in of the image plane, illustration of the high spatial resolution. Sub-illustration C: zoom-in of the angular plane in a low reflection region of the volume where the zoom-in illustration (but not the background) area has highly amplified tone values, to facilitate the study of the low-reflectance areas. Note the low level of distortion and noise, despite the high amplification. Sub-illustration D: zoom-in of the angular plane in a high reflectance region where the zoom-in illustration (but not the background) area has highly attenuated tone values, to facilitate the study of the high-reflectance areas. Note the graceful gradation of the tone values despite the high reflectance, indicating that the characterization is not suffering saturation. If a (large) number of positions have had an equal and in the illustration maximal intensity, it had been an indication (but not an evidence) that the characterization was suffering saturation. That is not the case in FIG. 4.

The figures illustrate the information which can be derived from utilizing the present invention. This information can be used in several different ways such as in improving the qualitative properties of the studied sample. It may deal a wide range of different industries which can be exemplified by the two example areas of possible use, described below:

Applications within the paper industry. Detailed (spatially resolved) characterization of gloss as well as color would be a vital tool for professionals in the area of product development, because many print quality problems are related to both the gloss and color characteristics of paper.

Applications within the security document industry. The most potent optical security functions are currently the so called Optically Variable Devices (OVD), which distinctly change in appearance as a function of angular set up relative to the light source and the observer. OVDs are included e.g. in bank notes (of high denominations) of the most dominating currencies, in personal identification documents, and in credit cards. The ability to perform detailed instrumental characterization of the relevant features of these OVDs would be of high value to the industry.

These are only two of a myriad of areas in which the present art do not meet the needs of the industries, and in which the present invention makes a significant contribution to meet these needs of the industries.

What is claimed is:

1. A method of obtaining high dynamic range, spectrally, spatially and angularly resolved radiance of a sample surface of a sample, said method comprising the steps of:
   a) irradiating electromagnetic radiation of controlled spectral distribution from at least one electromagnetic irradiator onto a sample surface of a sample and, using at least one electromagnetic sensitive sensor to register reflected spectral distribution;
   b) reflecting spectral distribution of an intensity of an electromagnetic field by a plurality of part-surfaces of the sample surface of the sample; and
   c) registering exposure time-period being selected individually for the sensor to compile an information volume that represents a registered high dynamic range spectrally resolved electromagnetic radiance as a function of a position of the part-surfaces within the sample surface of the sample and of a respective angle enforced upon the sample during measurement;

wherein a functional dependency between input radiation and output signal is achieved by at least one calibration being characterization of a response curve of the sensor;

wherein the calibration further comprising characterization of the response of the sensor as a function of the exposure time of the sensor, and characterization of error spatial propagation of individual saturated sensor element.

2. The method according to claim 1, wherein the characterization of the response curve of the sensor is approximated by a characterization of:
   i) a dark current, characterizing b in the relation $f(x) \approx mx+b$; and
   ii) slope optimizing m for the relation $f(x) \approx mx+b$, such that the function $z(x)=abs(f(x)-(mx+b))$ where $abs(\ )$ is the absolute value, is minimized when integrated over x.

3. The method according to claim 2, wherein characterization of the dark current is realized by measuring the sensor output while shielding the sensor from radiation of wavelengths that the sensor is sensitive to, after which the dark current characterization is thereafter used for compensation of the sensor output, the sensor output being reduced by values of the dark current of the sensor.

4. The method according to claim 3, wherein the characterization of the response of the sensor as a function of the exposure time of the sensor is performed by the following procedure:
   A) choosing a shortest possible exposure time, adjust radiation intensity onto the sensor to reach a low, dark current reduced, sensor output, in a range of 3-5 percent of a peak output;
   B) holding the radiation intensity constant during the following procedure steps;
   C) increasing the exposure time in increments and registering the sensor output; and
   D) stopping when the sensor output is saturated, and eliminate the corresponding exposure time-sensor output pair.

5. The method according to claim 4, wherein the error spatial propagation characterization is facilitated by separating the error spatial propagation characterization task in two causes of the error spatial propagation, circuit caused error spatial propagation, and scattering caused error propagation.

6. The method according to claim 5, wherein repetitive characterizations, distinguished in that a mid-point wavelengths of a spectrally well-defined narrow bandwidth electromagnetic radiation is varied between the characterizations, yielding a radiance factor matrix for each individual part-surfaces at each enforced angle characterized.

7. The method according to claim 6 further comprising the step of:
   d) polarizing the electromagnetic radiation irradiated by the irradiator by being passed through a polarization filter.

8. The method according to claim 7 further comprising the step of:
   e) passing the reflected and emitted spectral radiation from the sample surface of the sample through a polarization filter before being registered by the electromagnetic sensitive sensor.

9. The method according to claim 8, wherein repetitive characterizations, distinguished in that the mid-point wavelengths of the spectrally well-defined narrow bandwidth electromagnetic radiation is varied with maximally 10 nm between the characterizations, yielding a radiance factor matrix for each individual part-surfaces at each enforced angle characterized.

10. A method of obtaining high dynamic range, spectrally, spatially and angularly resolved radiance of a sample surface of a sample, said method comprising the steps of:
    a) irradiating electromagnetic radiation of controlled spectral distribution from at least one electromagnetic irradiator onto a sample surface of a sample and, using at least one electromagnetic sensitive sensor to register reflected spectral distribution;
    b) reflecting spectral distribution of an intensity of an electromagnetic field by a plurality of part-surfaces of the sample surface of the sample;
    c) registering exposure time-period being selected individually for the sensor to compile an information volume that represents a registered high dynamic range spectrally resolved electromagnetic radiance as a function of a position of the part-surfaces within the sample surface of the sample and of a respective angle enforced upon the sample during measurement; and
    d) selecting the exposure time-period by a functional dependency between input radiation and output signal being achieved by at least the following characterizations:
        1) characterization of a response curve of the sensor, which is approximated by a characterization of:
            i) a dark current, characterizing b in the relation $f(x) \approx mx+b$; and
            ii) slope optimizing m for the relation $f(x) \approx mx+b$, such that the function $z(x)=abs(f(x)-(mx+b))$ where $abs(\ )$ is the absolute value, is minimized when integrated over x;
        2) characterization of the response of the sensor as a function of the exposure time of the sensor; and
        3) characterization of error spatial propagation of individual saturated sensor element.

11. The method according to claim 10, wherein characterization of the dark current is realized by measuring the sensor output while shielding the sensor from radiation of wavelengths that the sensor is sensitive to, after which the dark current characterization is thereafter used for compensation of the sensor output, the sensor output being reduced by values of the dark current of the sensor.

12. The method according to claim 11, wherein the characterization of the response of the sensor as a function of the exposure time of the sensor is performed by the following procedure:
    A) choosing a shortest possible exposure time, adjust radiation intensity onto the sensor to reach a low, dark current reduced, sensor output, in a range of 3-5 percent of a peak output;
    B) holding the radiation intensity constant during the following procedure steps;
    C) increasing the exposure time in increments and registering the sensor output; and
    D) stopping when the sensor output is saturated, and eliminate the corresponding exposure time-sensor output pair.

13. The method according to claim 12, wherein the error spatial propagation characterization is facilitated by separating the error spatial propagation characterization task in two causes of the error spatial propagation, circuit caused error spatial propagation, and scattering caused error propagation.

14. The method according to claim 13, wherein repetitive characterizations, distinguished in that a mid-point wavelengths of a spectrally well-defined narrow bandwidth electromagnetic radiation is varied between the characterizations, yielding a radiance factor matrix for each individual part-surfaces at each enforced angle characterized.

15. The method according to claim 14 further comprising the step of:
   e) polarizing the electromagnetic radiation irradiated by the irradiator by being passed through a polarization filter.

16. The method according to claim 15 further comprising the step of:
   f) passing the reflected and emitted spectral radiation from the sample surface of the sample through a polarization filter before being registered by the electromagnetic sensitive sensor.

17. The method according to claim 16, wherein repetitive characterizations, distinguished in that the mid-point wavelengths of the spectrally well-defined narrow bandwidth electromagnetic radiation is varied with maximally 10 nm between the characterizations, yielding a radiance factor matrix for each individual part-surfaces at each enforced angle characterized.

18. A method of obtaining high dynamic range, spectrally, spatially and angularly resolved radiance of a sample surface of a sample, said method comprising the steps of:
   a) irradiating electromagnetic radiation of controlled spectral distribution from at least one electromagnetic irradiator onto a sample surface of a sample and, using at least one electromagnetic sensitive sensor to register reflected spectral distribution;
   b) reflecting spectral distribution of an intensity of an electromagnetic field by a plurality of part-surfaces of the sample surface of the sample;
   c) registering exposure time-period being selected individually for the sensor to compile an information volume that represents a registered high dynamic range spectrally resolved electromagnetic radiance as a function of a position of the part-surfaces within the sample surface of the sample and of a respective angle enforced upon the sample during measurement; and
   d) selecting the exposure time-period by a functional dependency between input radiation and output signal being achieved by at least the following characterizations:
   1) characterization of a response curve of the sensor, which is approximated by a characterization of:
      i) a dark current, characterizing b in the relation $f(x) \approx mx+b$; and
      ii) slope optimizing m for the relation $f(x) \approx mx+b$, such that the function $z(x)=abs(f(x)-(mx+b))$ where abs( ) is the absolute value, is minimized when integrated over x;
   2) characterization of the response of the sensor as a function of the exposure time of the sensor, the characterization of the response is performed by the at least the following procedure:
      A) choosing a shortest possible exposure time, adjust radiation intensity onto the sensor to reach a low, dark current reduced, sensor output, in a range of 3-5 percent of a peak output;
      B) holding the radiation intensity constant during the following procedure steps;
      C) increasing the exposure time in increments and registering the sensor output; and
      D) stopping when the sensor output is saturated, and eliminate the corresponding exposure time-sensor output pair;
   3) characterization of error spatial propagation of individual saturated sensor element; and
   e) polarizing the electromagnetic radiation irradiated by the irradiator by being passed through a polarization filter;
   wherein characterization of the dark current is realized by measuring the sensor output while shielding the sensor from radiation of wavelengths that the sensor is sensitive to, after which the dark current characterization is thereafter used for compensation of the sensor output, the sensor output being reduced by values of the dark current of the sensor.

19. The method according to claim 18 further comprising the step of:
   f) passing the reflected and emitted spectral radiation from the sample surface of the sample through a polarization filter before being registered by the electromagnetic sensitive sensor.

* * * * *